(12) United States Patent
Infranger et al.

(10) Patent No.: US 10,342,930 B1
(45) Date of Patent: Jul. 9, 2019

(54) PROTECTIVE COVER FOR A SYRINGE NEEDLE

(71) Applicant: Verena Solutions LLC, Chicago, IL (US)

(72) Inventors: Michael Infranger, Chicago, IL (US); Joseph Gambino, Chicago, IL (US)

(73) Assignee: Verena Solutions LLC, Chicago, IL (US)

( * ) Notice: Subject to any disclaimer, the term of this patent is extended or adjusted under 35 U.S.C. 154(b) by 0 days.

(21) Appl. No.: 15/063,724

(22) Filed: Mar. 8, 2016

Related U.S. Application Data

(63) Continuation-in-part of application No. 14/071,685, filed on Nov. 5, 2013, now Pat. No. 9,682,196, which is a continuation-in-part of application No. 13/214,474, filed on Jan. 9, 2012, now abandoned.

(51) Int. Cl.
*A61M 5/32* (2006.01)

(52) U.S. Cl.
CPC ........ *A61M 5/3243* (2013.01); *A61M 5/3257* (2013.01)

(58) Field of Classification Search
CPC .. A61M 5/3243; A61M 5/3257; A61M 5/322; A61M 5/32; A61M 5/3206
See application file for complete search history.

(56) References Cited

U.S. PATENT DOCUMENTS

| | | | |
|---|---|---|---|
| 3,605,744 A | 9/1971 | Dwyer | |
| 3,820,652 A | 6/1974 | Thackston | |
| 4,917,669 A * | 4/1990 | Bonaldo | A61M 25/0631 604/192 |
| 4,943,282 A | 7/1990 | Page et al. | |
| 4,994,045 A * | 2/1991 | Ranford | A61M 5/3271 604/198 |
| 5,112,307 A * | 5/1992 | Haber | A61M 5/24 604/110 |
| 5,137,524 A | 8/1992 | Lynn et al. | |
| 5,222,502 A | 6/1993 | Kurose | |
| 5,232,457 A | 8/1993 | Grim | |
| 5,405,326 A * | 4/1995 | Haber | A61M 5/345 604/110 |
| 6,485,469 B1 | 11/2002 | Steward et al. | |
| 8,721,546 B2 | 5/2014 | Belson | |
| 2005/0038399 A1 | 2/2005 | Suzuki et al. | |
| 2006/0282044 A1 * | 12/2006 | Mohammed | A61M 5/3232 604/192 |

* cited by examiner

*Primary Examiner* — Yogesh P Patel
(74) *Attorney, Agent, or Firm* — Andrus Intellectual Property Law, LLP

(57) ABSTRACT

A protective cover for a syringe needle includes a sheath and a needle hub. The sheath preferably includes a cylindrical body terminated with a bullet shaped end. The needle hub includes a needle base and a hypodermic needle retained in the needle base. The needle base includes a bullet shape and a locking projection extending from an outer perimeter of the needle base. A lengthwise slot is formed through the cylindrical body. The lengthwise slot receives a button portion of the locking projection. A retracted locking notch is formed on one end of the extension slot. An extended locking notch is formed on an opposing end of the lengthwise slot. The button portion is retained in the retracted locking notch or the extended locking notch. A second embodiment of the protective cover includes a sheath and a needle hub. The needle hub is slidably retained in the sheath.

20 Claims, 9 Drawing Sheets

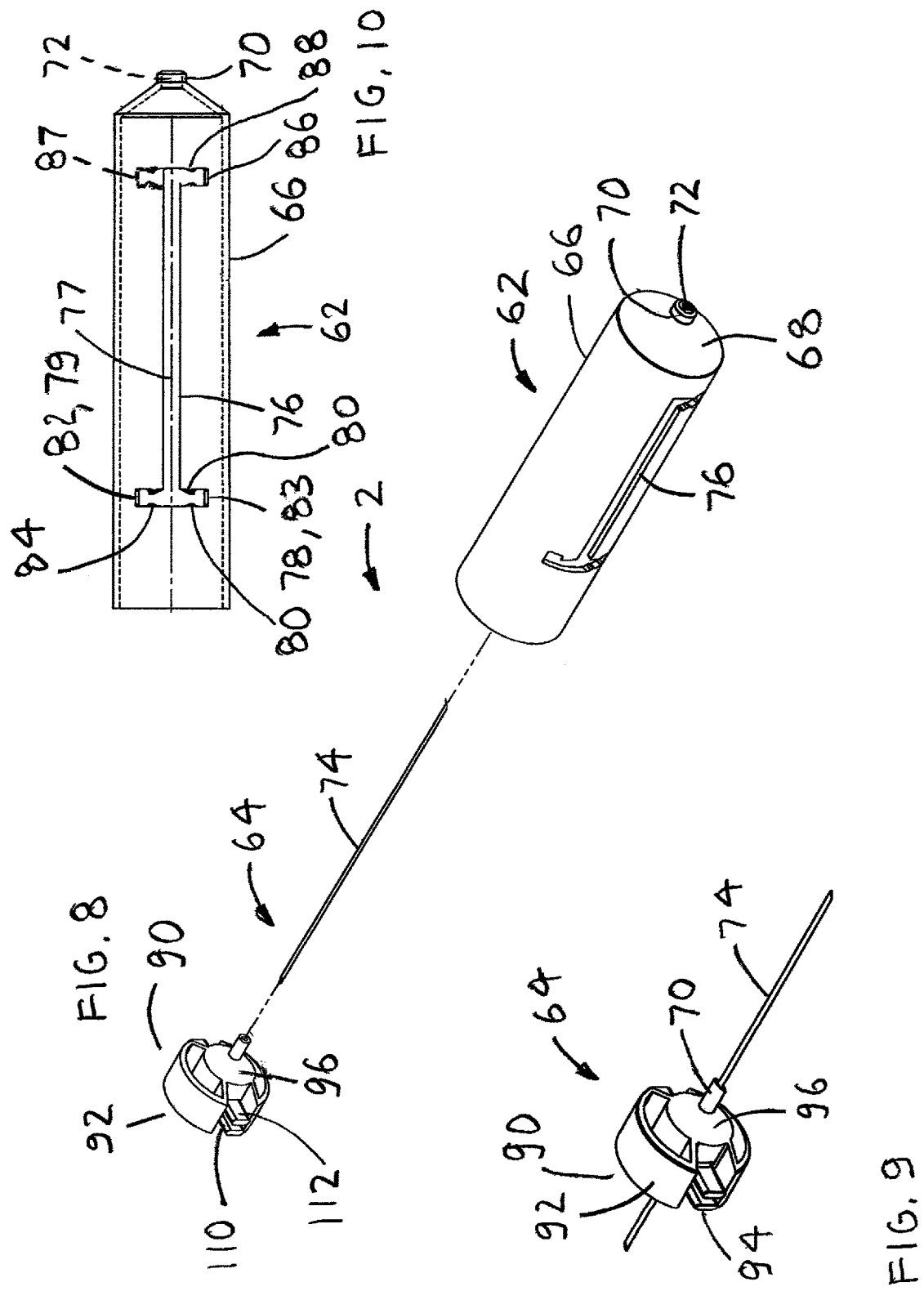

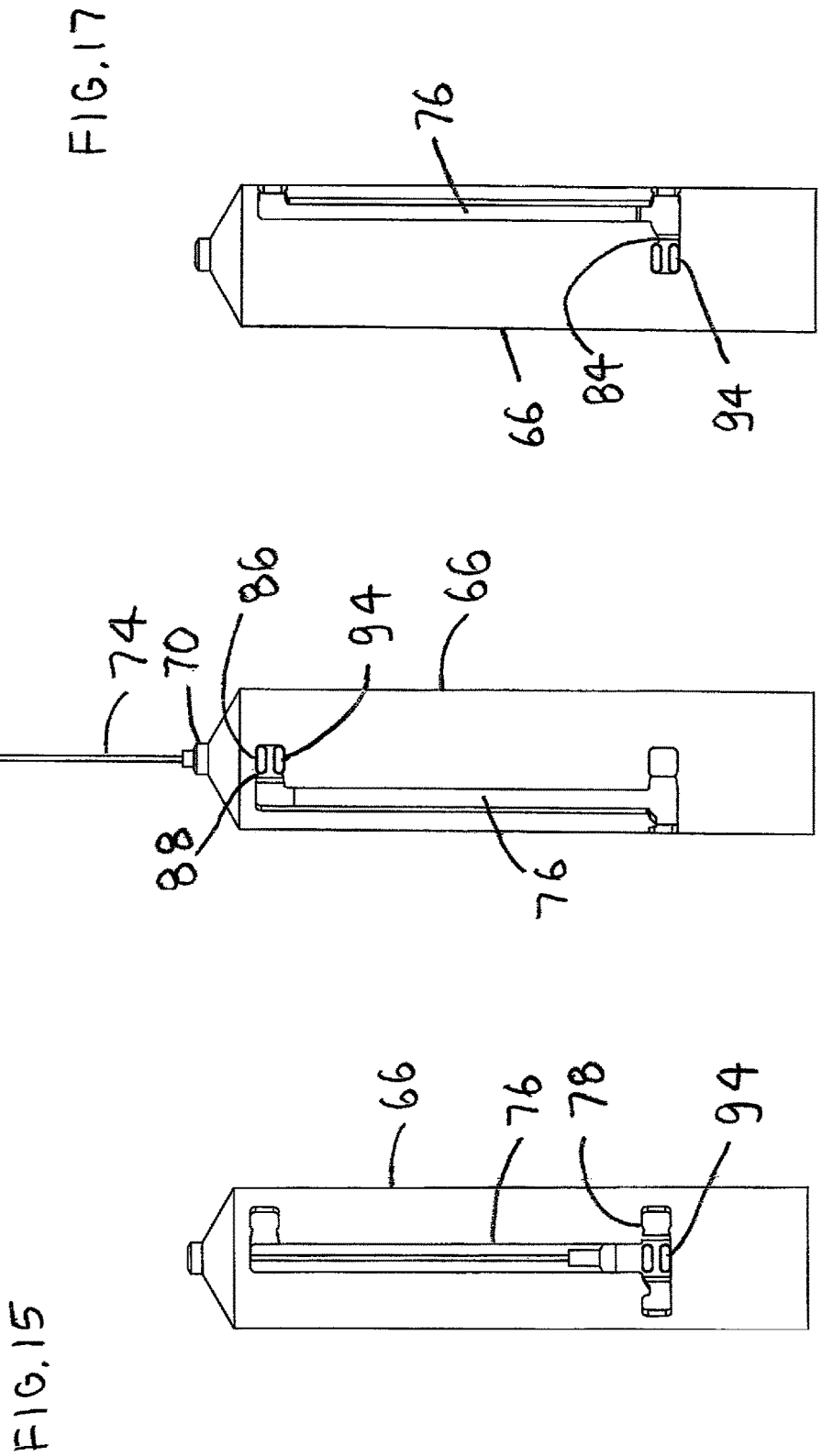

PROTECTIVE COVER FOR A SYRINGE NEEDLE

CROSS-REFERENCES TO RELATED APPLICATIONS

This is a continuation-in-part application, which takes priority from continuation-in-part patent application Ser. No. 14/071,685 filed on Nov. 5, 2013, which takes priority from patent application Ser. No. 13/214,474 filed on Jan. 9 2012.

BACKGROUND OF THE INVENTION

Field of the Invention

The present invention relates generally to syringes and more specifically to a protective cover for a syringe needle, which reduces the risk of injury due to accidental needle pricks.

Discussion of the Prior Art

In providing medical care for patients, anesthesia is routinely necessary. Anesthesia allows medical professionals to perform complex medical procedures, while the patient is in a sedated state allowing the medical professional more freedom to operate, and minimizing the pain felt by the patient. Anesthesia is usually administered via a non-disposable syringe, through a disposable needle.

The syringes used to administer local anesthetics use a disposable cartridge of local anesthetic and a disposable needle, which attaches to an end of the syringe. The disposable needle is supplied by the manufacturer with a two part protective cover. The back part of the cover fits over the mounting hub of the needle and extends one centimeter past a back end of the front cover and is removed when the syringe is loaded for use. The front portion remains as a protective cover to preserve the sterility of the needle and to protect a user, while handling the syringe prior to and after use. The front portion of the protective cover is referred to as a "needle cap," because of the manner in which the back portion of the cover telescopes over the front portion and the two are sealed together, an annular ridge or shoulder is created one centimeter from the back end of the front portion of the cap. All commercially available needles for dental office use at this time have a similar ridge or shoulder as the apparatus used to attach the needle to most dental syringes is the same. The needles and their protective needle caps intended for use in dental offices are supplied in different lengths for use in Mandibular and Maxillary injections. The Mandibular needle cap is 4.5 to 5 centimeters long from the previously mentioned shoulder to the front end and the Maxillary needle cap is 3 to 3.5 centimeters long between those points. The diameter of the cap at the shoulder is 1 centimeter and immediately behind the shoulder the diameter is less, usually 0.85 centimeters.

The needle cap is removed immediately prior to administering the injection to the patient. The danger of an infectious needle stick occurs when the protective needle cap is replaced on the needle, post injection, which is now contaminated with the patient's blood and saliva. A single method dominates the dental field and it includes a two handed process. The syringe is normally held in the operator's favored hand and the needle cap is held in the other. The cap and needle are then slowly brought together, until the cap has sufficiently covered the needle and locked into place at the junction of the needle and syringe. If the needle misses the opening in the cap, there is a significant chance that the hand holding the cap will be stuck and the operator exposed to any blood-borne infection carried by the patient.

To avoid this problem, the Center for Disease Control currently recommends discarding disposable syringes without replacing the needle cap. This is impractical in a dental office because only the needle, the covers, and the anesthetic capsule (or cartridge) are disposable; the remainder of the syringe is sterilized and reloaded. Often a needle is used multiple times on a single patient to administer additional anesthetic. Though the risk of an accidental stick is greater handling the uncapped syringe needle than the risk to recap the needle, needles are still reused to save time and money.

There are techniques for handling the recapping procedure to avoid the danger of a stick such as the "scooping" the cap off a table top, commonly called the 'one-handed scoop method' with the needle and pressing the cap against a wall to seat the cap on the needle base or holding the cap with a hemostat or forceps instead of the hand. These techniques work, but they are awkward at best, allow for the risk of picking up spatter, which might have fallen onto the dental tray and often ignored out of convenience. Moreover the method name is a misnomer; it in fact does require a second hand to fasten the cap securely to the needle hub once it is in place. While this method is commonly taught in dental schools, it is rarely used by tenured dentists in favor of the two-handed technique.

U.S. Pat. No. 3,605,744 to Dwyer discloses an injection apparatus and method of injection. U.S. Pat. No. 3,820,652 to Thackston discloses a packaged syringe construction. U.S. Pat. No. 5,222,502 to Kurose discloses a blood collecting needle. U.S. Pat. No. 6,485,469 to Steward et al. discloses a shielded dental safety needle.

Accordingly, there is a clearly felt need in the art for a protective cover for a syringe needle, which reduces the risk of injury due to exposure to blood borne pathogens, because of accidental needle stick injuries incurred, while attempting to recap a syringe needle.

SUMMARY OF THE INVENTION

The present invention provides a protective cover for a syringe needle, which reduces the risk of injury due to accidental needle pricks. The protective cover for a syringe needle includes a sheath and a needle hub. The sheath preferably includes a cylindrical body, which is terminated with a hollow bullet shaped end. A needle opening is formed through a center of the hollow bullet shaped end to provide clearance for a syringe needle. The needle hub includes a needle base and a hypodermic needle. The hypodermic needle is retained in the needle base. An outer perimeter of the needle base is sized to be received by an inner perimeter of the cylindrical body and the bullet shaped end. The needle base includes a bullet shape and a locking projection extending from an outer perimeter of the needle base.

A lengthwise slot is formed through a front of the cylindrical body. The lengthwise slot extends substantially a length of said cylindrical body. The lengthwise slot is sized to receive a button portion of the locking projection. A retracted locking notch is formed on one end of the extension slot. A retracted locking finger extends into the retracted locking notch to retain the button portion of the locking projection, such that the syringe needle cannot accidentally prick a user. An extended locking notch is formed on an opposing end of the lengthwise slot. An extended locking finger extends into the extended locking notch to retain the button portion of the locking projection, such that the syringe needle may be used. A storage notch is formed on the one end of the extension slot and opposite the retracted locking notch. A storage finger extends into the storage notch to retain the locking projection of the needle base, such that the syringe needle may not be used again. A view window is preferably formed through the cylindrical body opposite the extension slot.

In use, the locking projection is snapped out of the retracted locking finger and pushed into the lengthwise slot. The button portion is slid to the other end of the lengthwise slot. The button portion is then pushed into the extended locking notch and the syringe needle is locked in an extended position by pushing the button portion into the extended locking finger. After the syringe needle has been used, the button portion is slid back into the lengthwise slot and pushed to the one end of the lengthwise projection. The locking projection is pushed into the storage notch to prevent the syringe needle from being reused.

A second embodiment of the protective cover for a syringe needle preferably includes a sheath and a needle hub. The sheath preferably includes a cylindrical body, which is terminated with a conical shaped end. A needle opening is formed through a center of the conical shaped end to provide clearance for a syringe needle. A first lengthwise slot is formed through one side of the cylindrical body and a second lengthwise slot is formed through an opposing side of the cylindrical body. A bottom of each lengthwise slot is preferably terminated with a retracted lock slot extending substantially perpendicular to a lengthwise axis of the lengthwise slot in one direction. A permanent lock slot is preferably formed in a direct opposite to the retracted lock slot. A top of each lengthwise slot is terminated with an extended lock slot, which extends substantially perpendicular to the lengthwise axis of the lengthwise slot.

The needle hub includes a needle base and a hypodermic needle. The hypodermic needle is retained in the needle base. The needle base preferably includes an outer perimeter, a first lock tab, a second lock tab, a conical end and a syringe threaded tap. The outer perimeter includes a substantially round shape. The conical end is formed in one end of the needle base and the syringe threaded tap is formed in an opposing end of the needle base. A pair of opposing grooves are formed in the outer perimeter. The first and second lock tabs extend from a bottom of the pair of opposing grooves. The first and second lock tabs extend past the outer perimeter of the needle base. The outer perimeter of the needle base is sized to be slidably received by an inner perimeter of the cylindrical body. The conical shaped end of the cylindrical body is shaped to receive the conical end of the needle base.

In use, the second embodiment of the protective cover for a syringe needle comes with the first and second lock tabs retained in the first and second lock slots. A threaded end of a syringe is threaded into the syringe threaded tap. A health care professional (user) holds a body of the syringe with one hand and the opposing hand is used to hold the second embodiment of the protective cover for a syringe needle. The user twists the cylindrical body relative to the syringe, such that the first and second lock tabs become positioned in the first and second lengthwise slot. The cylindrical body and the syringe are pushed toward each other, until the hypodermic needle is full exposed. The user then twists the cylindrical body until the first and second lock tabs are retained in the first and second extended lock slots. The syringe may now be used to dispense the contents therein. After dispensing the syringe contents, the cylindrical body is twisted, such that the first and second tabs are positioned in the first and second lengthwise slots. The cylindrical body is pulled away from the syringe. Finally, the cylindrical body is twisted, such that the first and second tabs are locked in the permanent lock slot.

Accordingly, it is an object of the present invention to provide a protective cover for a syringe, which reduces the risk of injury due to exposure to blood borne pathogens, because of accidental needle stick injuries incurred, while attempting to recap syringe needles.

These and additional objects, advantages, features and benefits of the present invention will become apparent from the following specification.

BRIEF DESCRIPTION OF THE DRAWINGS

FIG. 8 is an exploded perspective view of a second embodiment of a protective cover for a syringe needle in accordance with the present invention.

FIG. 9 is a perspective view of a needle hub of a second embodiment of a protective cover for a syringe needle in accordance with the present invention.

FIG. 10 is a side view of a sheath of a second embodiment of a protective cover for a syringe needle in accordance with the present invention.

FIG. 15 is a side view of a second embodiment of a protective cover for a syringe needle with a lock tab positioned at a bottom of a lengthwise slot in accordance with the present invention.

FIG. 16 is a side view of a second embodiment of a protective cover for a syringe needle with a lock tab retained in an extended lock slot in accordance with the present invention.

FIG. 17 is a side view of a second embodiment of a protective cover for a syringe needle with a lock tab retained in a permanent lock slot in accordance with the present invention.

DETAILED DESCRIPTION OF THE PREFERRED EMBODIMENTS

Figure 1:
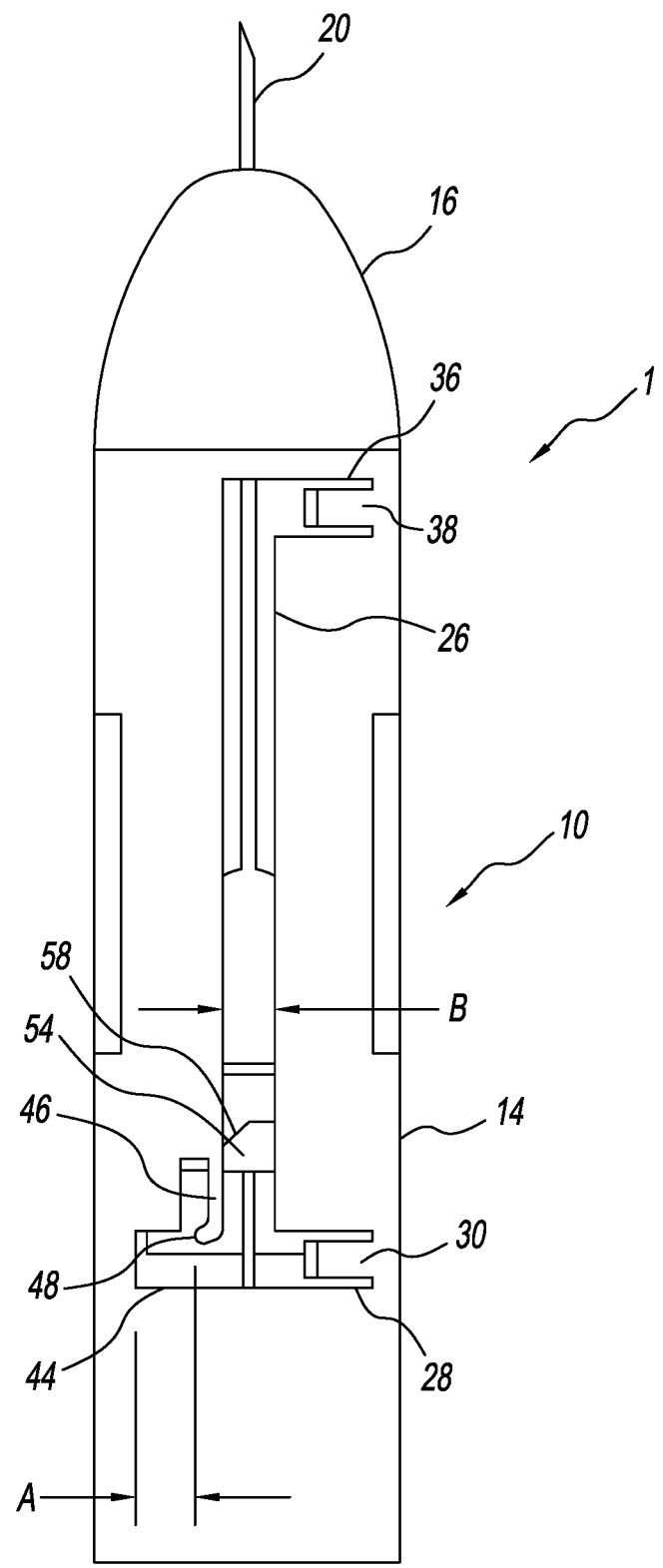
FIG. 1 is a front view of a protective cover for a syringe with a syringe needle partially extended in accordance with the present invention.
Figure 2:
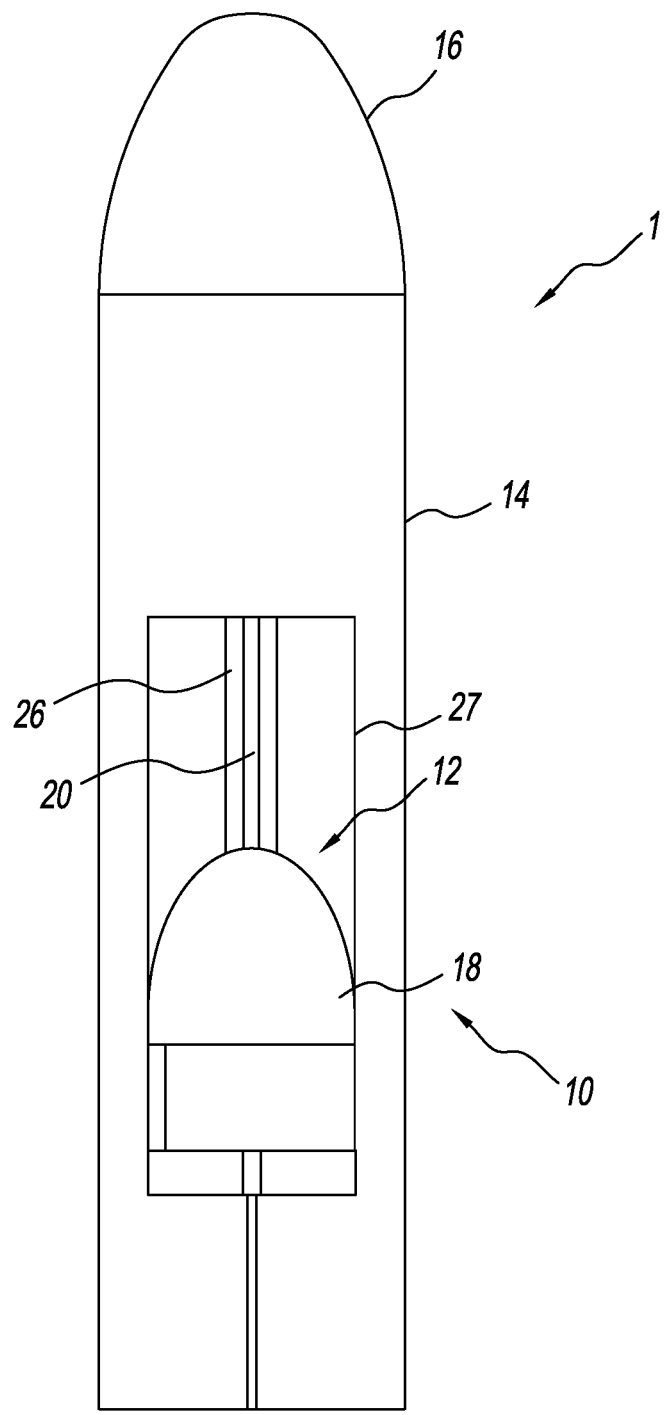
FIG. 2 is a rear view of a protective cover for a syringe with a syringe needle retracted in accordance with the present invention.
Figure 5:
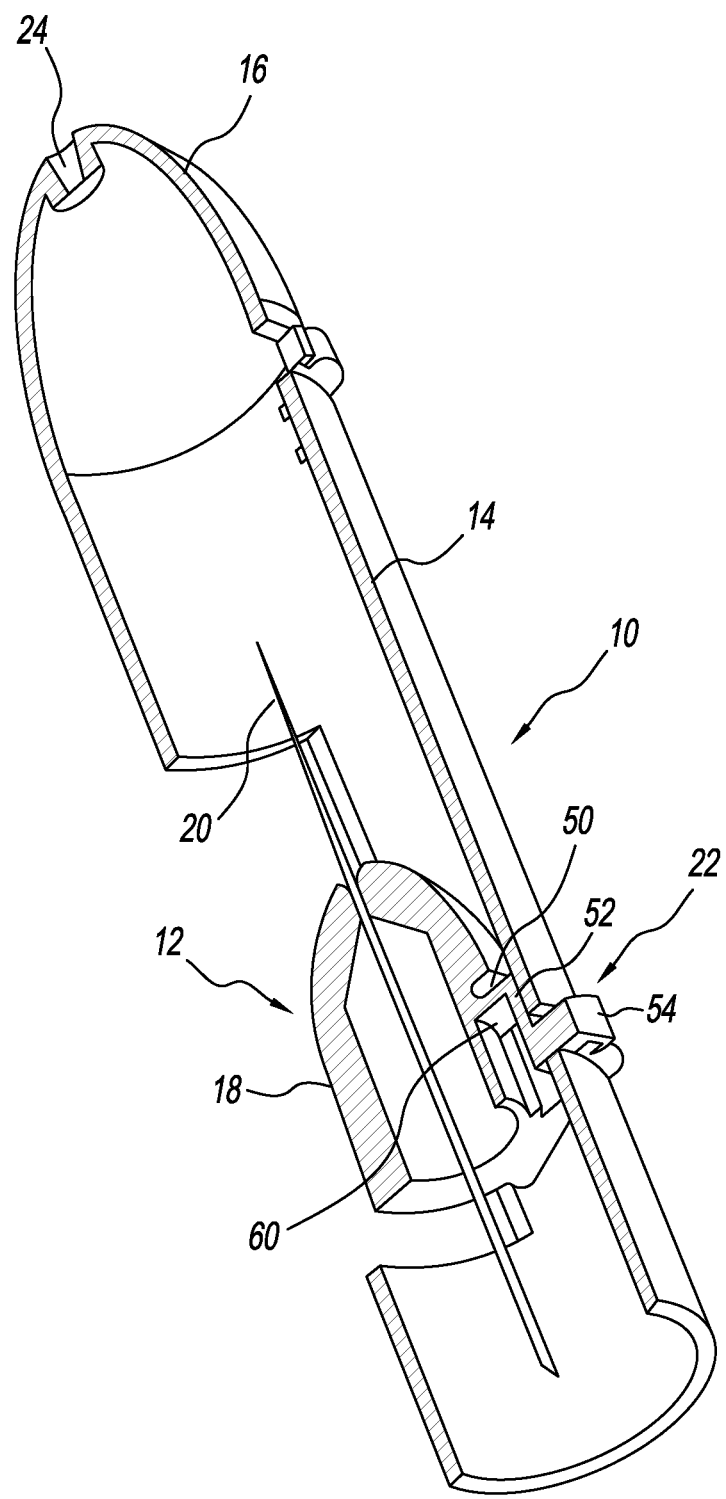
FIG. 5 is a perspective cross section view of a protective cover for a syringe needle with the syringe needle locked in a retracted position in accordance with the present invention.

With reference now to the drawings, and particularly to FIG. 1, there is shown a front view of a protective cover for a syringe needle 1. With reference to FIGS. 2 and 5, the protective cover for a syringe needle 1 includes a sheath 10 and a needle hub 12. The sheath 10 preferably includes a cylindrical body 14 and a hollow bullet shaped end 16. The cylindrical body 14 is terminated with the hollow bullet shaped end 16. The needle hub 12 includes a needle base 18, a hypodermic needle 20 and a locking projection 22. The needle base 18 has a substantial bullet shape. An outer perimeter of the needle base 18 is sized to be received by an inner perimeter of the cylindrical body 14 and the hollow bullet shaped end 16. The hypodermic needle 20 is retained in a center of the bullet shaped base 18. The locking projection 22 extends from an outer perimeter of the bullet shaped base 18. A needle opening 24 is formed through a top of the hollow bullet shaped end 16 to provide clearance for the hypodermic needle 20.

A lengthwise slot 26 is formed through a front of the cylindrical body 14. The lengthwise slot 26 extends substantially a length of the cylindrical body 14. A view window 27 is preferably formed through the cylindrical body 14 opposite the extension slot 26 to provide a visual indication of a position of the needle base 18. The lengthwise slot 26 is sized to receive a button portion 54 of the locking projection 22. A retracted locking notch 28 extends from a side of the extension slot 26 at one end thereof.

Figure 6:
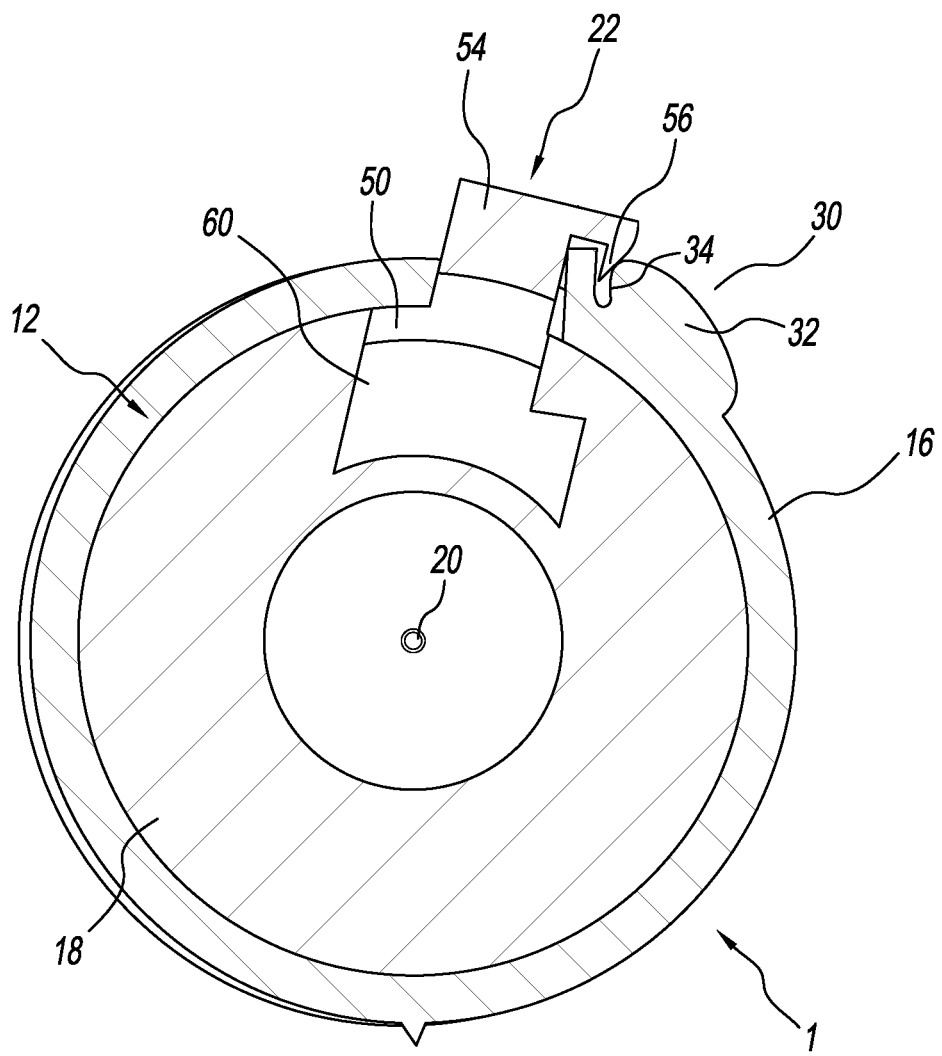
FIG. 6 is an end cross sectional view of a protective cover for a syringe needle with the syringe needle locked in a retracted position in accordance with the present invention.

With reference to FIG. 6, a retracted locking finger 30 extends into the retracted locking notch 28 to retain the button projection 54 of the locking projection 22, such that the hypodermic needle 20 cannot accidentally prick a user. The retracted locking finger 30 includes a contact portion 32 and a lock slot 34. The retracted locking finger 30 is formed as an integral portion of the cylindrical body 16. The lock slot 34 retains a locking extension 56 of the button portion 54. The contact portion 32 extends outward from a perimeter of the cylindrical body 16 to allow the retracted locking finger 30 to be depressed inward toward a center of the cylindrical body 16 to release the locking extension 56.

Figure 7:
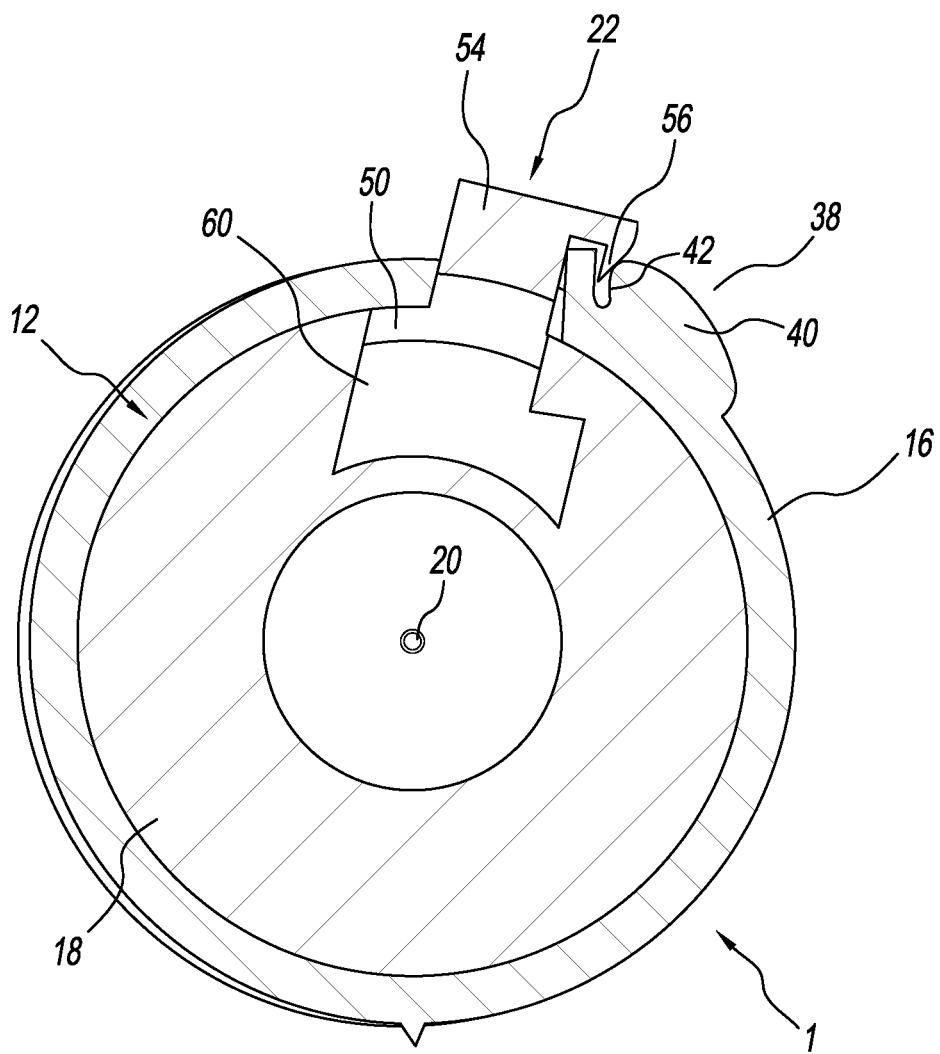
FIG. 7 is an end cross sectional view of a protective cover for a syringe needle with the syringe needle locked in an extended position in accordance with the present invention.

With reference to FIG. 7, an extended locking notch 36 extends from a side of the lengthwise slot 26 at an opposing end thereof. An extended locking finger 38 extends into the extended locking notch 36 to retain the button portion 54 of the locking projection 22, such that the hypodermic needle 20 may be used. The extended locking finger 38 includes a contact portion 40 and a lock slot 42. The extended locking finger 38 is formed as an integral portion of the cylindrical body 16. The lock slot 42 retains the locking extension 56. The contact portion 40 extends outward from a perimeter of the cylindrical body 16 to allow the extended locking finger 38 to be depressed inward toward a center of the cylindrical body 16 to release the locking extension 54.

A storage notch 44 is formed on the one end of the extension slot 26 and opposite the retracted locking notch 28. A storage finger 46 extends into the storage notch 44 to retain the locking projection 22 of the needle base 18, such that the hypodermic needle 20 may not be used again. The storage finger 46 is terminated with a lock portion 48. A distance "A" between the lock portion 48 and an end of the storage notch 44 is preferably greater than a width "B" of a button portion 54 to retain the button portion 54, such that the hypodermic needle 20 may not be used again, after the button portion has been pushed past the locking portion 48.

The locking projection 22 preferably includes a radial arm 50, an axial arm 52, the button portion 54 and the locking extension 56. The radial arm 50 extends outward from the needle base 18. The axial arm 52 extends outward from an end of the radial arm 50. The button portion 54 terminates an end of the axial arm 52. The button portion 54 is cantilevered relative to the needle base 18 through the radial arm 50 and the axial arm 52. A single cantilevered arm may used to replace the radial arm 50 and the axial arm 52. The locking extension 56 extends from the button portion 54 inward toward a center of the needle base 18. The locking extension 56 is sized to be received by the lock slots 34, 42. A chamfer 58 is formed on a side of the button portion 54 to allow the button portion 54 to be pushed past the lock portion 48. A projection cavity 60 is formed below the locking projection 22.

Figure 3:
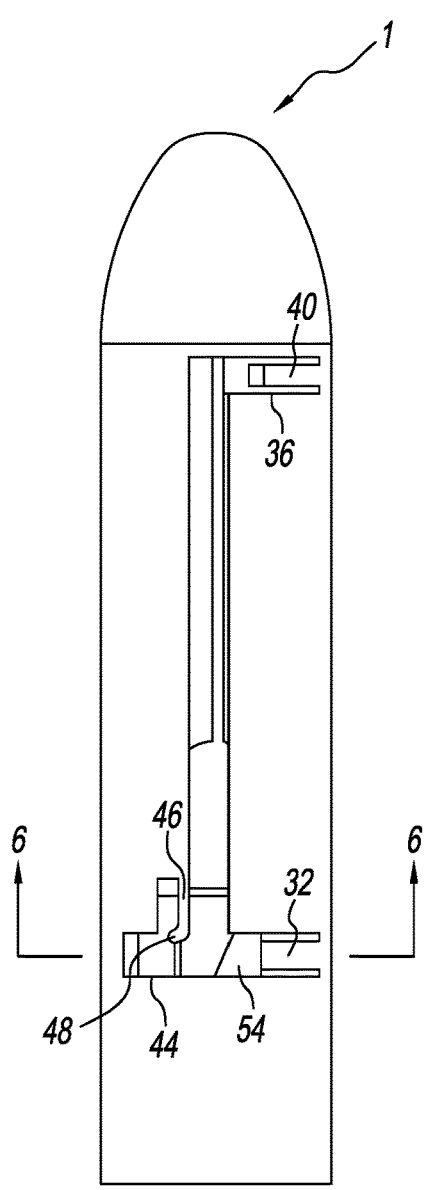
FIG. 3 is a front view of a protective cover for a syringe with the syringe needle locked in a retracted position in accordance with the present invention.
Figure 4:
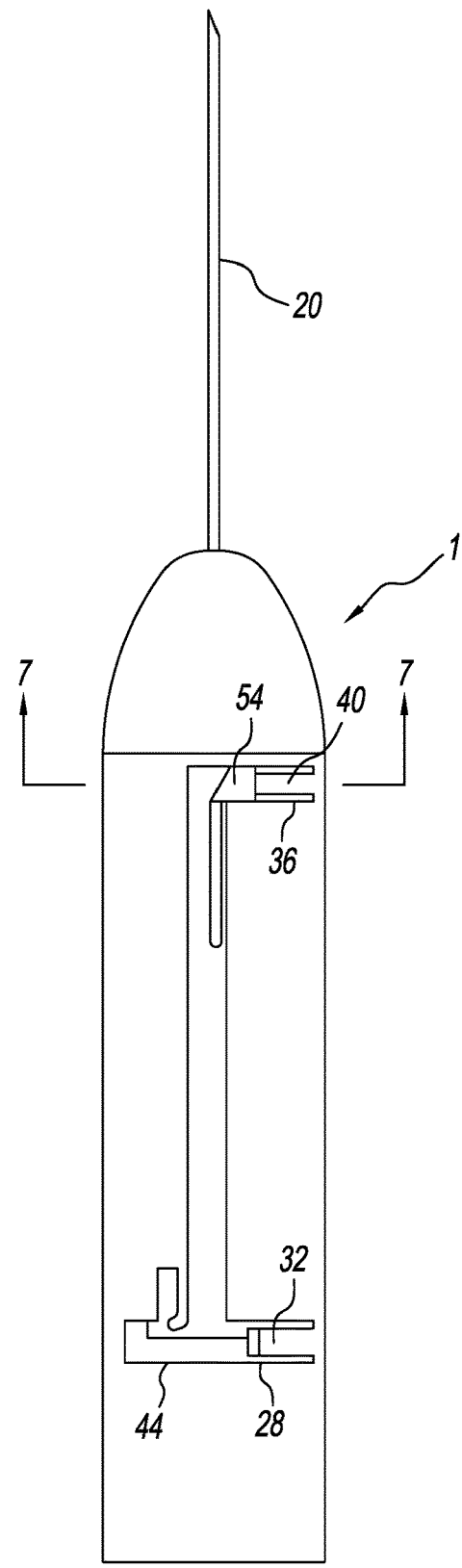
FIG. 4 is a front view of a protective cover for a syringe with the syringe needle locked in an extended position in accordance with the present invention.

With reference to FIGS. 3-4, the contact portion 32 of the retracted locking finger 30 is depressed with one hand and the button portion 54 of the locking projection 22 is slid out of the retracted locking notch 28 into the lengthwise slot 26 with the other hand. The button portion 54 of the locking projection 22 is slid to the other end of the lengthwise slot 26. The locking extension 56 of the locking projection 22 is then pushed into lock slot 42 of the extended locking finger 38 and the hypodermic needle 20 is locked in an extended position. After the hypodermic needle 20 has been used, the contact portion 40 is depressed with one hand and the button portion 54 is slid out of the extended locking notch 28 into the lengthwise slot 26 with the other hand. The button portion 54 is slid down the lengthwise slot 26 to the storage notch 44. The button portion 54 is pushed into the storage notch 44 past the lock portion 48 to prevent the hypodermic needle 20 from being reused.

With reference to FIGS. 8-10, a second embodiment of the protective cover for a syringe needle 2 preferably includes a sheath 62 and a needle hub 64. The sheath 62 preferably includes a cylindrical body 66, which is terminated with a conical shaped end 68. A needle guide 70 preferably extends from an end of the conical shaped end 68. A needle opening 72 is formed through a center of the needle guide 70 to provide support for a syringe needle 74. A first lengthwise slot 76 is formed through one side of the cylindrical body 66 and a second lengthwise slot 77 is formed through an opposing side of the cylindrical body 66. A bottom of the first and second lengthwise slots 76, 77 are preferably terminated with first and second retracted lock slots 78, 79 extending substantially perpendicular to a lengthwise axis of the first and second lengthwise slots 76, 77 in one direction. The first and second lock slots 78, 79 each include a lock projection 80 extending from at least one of a top and a bottom of the first and second lock slots 78, 79. First and second permanent lock slots 82, 83 are preferably formed in a direction opposite to said first and second lock slots 78, 79. The first and second permanent lock slots 82, 83 preferably include a permanent lock projection 84 extending from at least one of a top and a bottom of the first and second permanent lock slots 82, 83. A top of the first and second lengthwise slots 76, 77 are terminated with first and second extended lock slots 86, 87, which extend substantially perpendicular to the lengthwise axis of the lengthwise slot 76, 77. The first and second extended lock slots 86, 87 preferably include an extended lock projection 88 extending from at least one of a top and a bottom of the first and second extended lock slots 86, 87.

Figure 11:
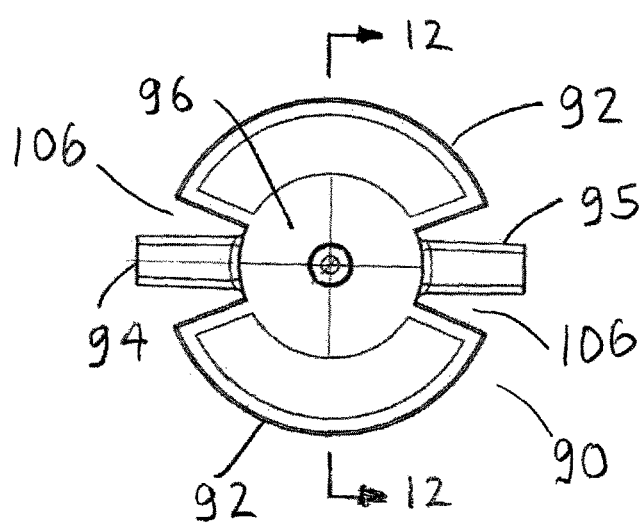
FIG. 11 is a top view of a needle base of a second embodiment of a protective cover for a syringe needle in accordance with the present invention.
Figure 12:
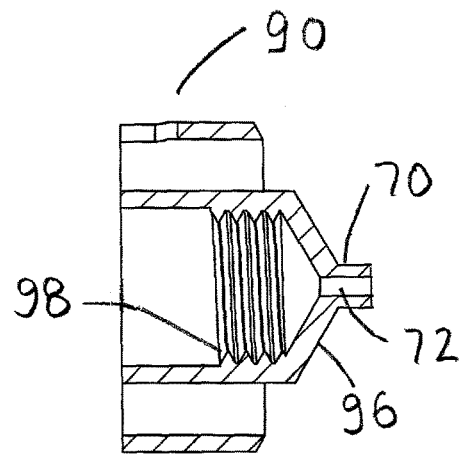
FIG. 12 is a cross sectional view of a needle base cut through FIG. 11 of a second embodiment of a protective cover for a syringe needle in accordance with the present invention.

With reference to FIGS. 11-12, the needle hub 64 includes a needle base 90 and the hypodermic needle 74. The hypodermic needle 74 is retained in the needle base 90. The hypodermic needle 74 extends past both ends of the needle base 90. The needle base 90 preferably includes an outer perimeter 92, a first lock tab 94, a second lock tab 95, a conical end 96 and a syringe threaded tap 98. The outer perimeter 92 includes a substantially round shape. Each lock tab 94 preferably includes two elements 110, 112, which are capable of flexing toward each other to move past the lock projections 80 and the extended lock projections 88. The conical end 96 is formed in one end of the needle base 90 and the syringe threaded tap 98 is formed in an opposing end of the needle base 90. A pair of opposing grooves 106 are formed in the outer perimeter 92. The first and second lock tabs 94, 95 extend from a bottom of the pair of opposing grooves 106. The first and second lock tabs 94, 95 extend past the outer perimeter 92 of the needle base 90. The outer perimeter 92 of the needle base 90 is sized to be slidably received by an inner perimeter of the cylindrical body 66. The conical shaped end 68 of the cylindrical body 66 is shaped to receive the conical end 96 of the needle base 90.

Figure 13:
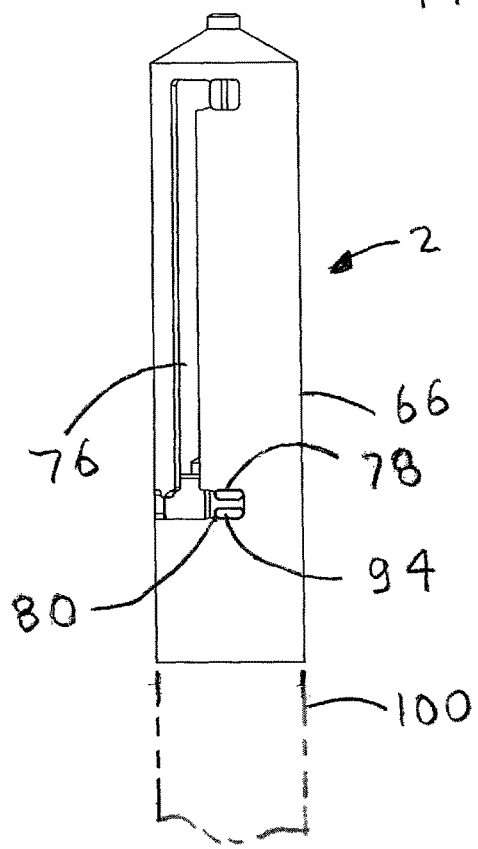
FIG. 13 is a side view of a second embodiment of a protective cover for a syringe needle in a locked position in accordance with the present invention.

With reference to FIG. 13, the protective cover for a syringe needle 2 is provided with the first and second lock tabs 94, 95 retained in the first and second lock slots 78, 79. The lock projection 80 prevents lateral movement of the first and second lock tabs 94, 95 in the first and second lock slots 78, 79. A threaded end of a syringe 100 is threaded into the syringe threaded tap 98. A health care professional (user) holds a body of the syringe 100 with one hand and the protective cover for a syringe needle 2 is held in the other hand.

Figure 14:
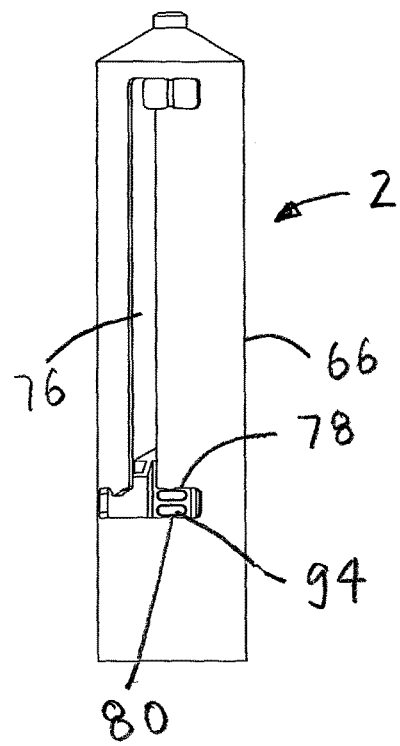
FIG. 14 is a side view of a second embodiment of a protective cover for a syringe needle with a lock tab positioned midway between a lock slot and a lengthwise slot in accordance with the present invention.

With reference to FIGS. 14-15, the user twists the cylindrical body 66 relative to the syringe 100, such that the first and second lock tabs 94, 95 move past the lock projection 80 into the first and second lengthwise slot 76, 77.

With reference to FIG. 16, the cylindrical body 66 and the syringe 100 are pushed toward each other, until the hypodermic needle 74 is full exposed. The user then twists the cylindrical body 66 until the first and second lock tabs 94, 95 are retained in the first and second extended lock slots 86, 87. The syringe 100 may now be used to dispense the contents therein. With reference to FIG. 17, after dispensing the syringe contents, the cylindrical body 66 is twisted, such that the first and second lock tabs 94, 95 are positioned in the first and second lengthwise slots 76, 77. The cylindrical body 66 is pulled away from the syringe 100. Finally, the cylindrical body 66 is twisted, such that the first and second lock tabs are locked in the permanent lock slots 82, 83. The permanent lock projection 84 prevents the first and second lock tabs 94, 95 from being removed from the permanent lock slots 82, 83.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

We claim:

1. A protective cover for a syringe needle comprising:
   a sheath comprising a cylindrical body with a pair of lengthwise slots, a retracted lock slot extending perpendicularly outward from a first end of each lengthwise slot, an extended lock slot extending perpendicularly outward from an opposing end of each lengthwise slot, and a permanent lock slot extending perpendicularly outward from the first end each lengthwise slot with a permanent lock projection extending into each permanent lock slot; and
   a needle hub located within the sheath comprising a needle and a needle base, wherein the needle base comprises an outer cylindrical perimeter, a pair of grooves extending interior of the outer cylindrical perimeter to an interior cylindrical wall, and a pair of tabs that extend from the interior cylindrical wall through the pair of grooves and into the lengthwise slots; and
   wherein the tabs can be slid along the lengthwise slots into positions adjacent the retracted lock slots, the extended lock slots, or the permanent lock slots, each tab of the pair of tabs comprises two elements oriented perpendicular to the lengthwise slots and parallel to each permanent lock slot, the two elements spaced apart such as to each engage the cylindrical body when positioned within the permanent lock slot, wherein the elements are inwardly flexible towards one another.

2. The protective cover of claim 1, wherein sliding the tabs through the lengthwise slots towards the extended lock slots extends the needle from the sheath and sliding the tabs through the lengthwise slots towards the retracted lock slots retracts the needle into the sheath.

3. The protective cover of claim 2, wherein the cylindrical body is terminated with a bullet shaped end or a conical shaped end.

4. The protective cover of claim 3, wherein a needle opening is formed through a center of the bullet shaped end or the conical shaped end.

5. The protective cover of claim 1, wherein slots extend substantially a length of the cylindrical body.

6. The protective cover of claim 1, wherein the lengthwise slots are positioned on opposite sides of the cylindrical body.

7. The protective cover of claim 1, wherein an element of each of the tabs simultaneously engages the cylindrical body and the permanent lock projection when the tabs are secured within the permanent lock slots.

8. The protective cover of claim 7, wherein the permanent lock projections each comprise a ramp that extends away from a respective lengthwise slot and an inner face oriented parallel to the lengthwise slots, wherein an element of each of the tabs engages the inner face of the permanent lock projection.

9. The protective cover of claim 8, wherein engagement between an element of each tab with the permanent lock projection inwardly flexes the element towards an other element of each tab to move the tabs past the permanent lock projections into the permanent lock slots.

10. The protective cover of claim 9, wherein once the elements move past the lock projections, the elements return away from the other elements to positions in engagement with the cylindrical body and the lock projection.

11. The protective cover of claim 9, wherein the permanent lock projection extending into each permanent lock slot is a first permanent lock projection and further comprising:
    a second permanent lock projection extending into each permanent lock slot wherein the other element of each tab engages the cylindrical body and the second permanent lock projection when positioned within the permanent lock slot.

12. The protective cover of claim 1, wherein an outer peri_mete of the needle base is sized to be received by an inner perimeter of the cylindrical body.

13. The protective cover of claim 1, wherein the needle extends from opposing ends of the needle base.

14. The protective cover of claim 1, herein the needle hub may be secured to a syringe.

15. The protective cover of claim 1, wherein the needle base further comprises a threaded tap to receive a threaded end of a syringe.

16. The protective cover of claim 15 wherein the interior cylindrical wall comprises the threaded tap.

17. The protective cover of claim 1, herein twisting the needle hub relative to the sheath pushes the tabs into the retracted lock slots or the extended lock slots.

18. The protective cover of claim 1, wherein pushing the tabs into the retracted lock slots locks the needle in a retracted position and pushing the tabs into the extended lock slots locks the needle in an extended position.

19. The protective cover of claim 1, wherein the permanent lock slots are located opposite the retracted lock slots on the same end of the lengthwise slots as the retracted lock slots.

20. The protective cover of claim 1, wherein pushing the tabs into the permanent lock slots permanently locks the needle in a retracted position so that the needle cannot be used again.

\* \* \* \* \*

UNITED STATES PATENT AND TRADEMARK OFFICE
CERTIFICATE OF CORRECTION

| | |
|---|---|
| PATENT NO. | : 10,342,930 B1 |
| APPLICATION NO. | : 15/063724 |
| DATED | : July 9, 2019 |
| INVENTOR(S) | : Infranger et al. |

It is certified that error appears in the above-identified patent and that said Letters Patent is hereby corrected as shown below:

In the Claims

In Claim 5, Column 8, Lines 40-41, the claim should read:
"The protective cover of claim 1, wherein the lengthwise slots extend substantially a length of the cylinder body."

Signed and Sealed this
Fourth Day of February, 2020

Andrei Iancu
*Director of the United States Patent and Trademark Office*

UNITED STATES PATENT AND TRADEMARK OFFICE
CERTIFICATE OF CORRECTION

PATENT NO. : 10,342,930 B1  
APPLICATION NO. : 15/063724  
DATED : July 9, 2019  
INVENTOR(S) : Michael Infanger and Joseph Gambino Page 1 of 1

It is certified that error appears in the above-identified patent and that said Letters Patent is hereby corrected as shown below:

On the Title Page

Item (72), The inventor's name should read -Michael Infanger-.

Signed and Sealed this  
Twenty-second Day of December, 2020

Andrei Iancu  
*Director of the United States Patent and Trademark Office*